United States Patent
Tian et al.

(10) Patent No.: US 10,968,440 B2
(45) Date of Patent: Apr. 6, 2021

(54) METHOD FOR HIGH-YIELD FERMENTATION OF RECOMBINANT PROLINE AMINOPEPTIDASE AND PREPARATION OF DEBITTERED RICE PEPTIDE

(71) Applicant: Jiangnan University, Wuxi (CN)

(72) Inventors: Yaping Tian, Wuxi (CN); Kaidao Wang, Wuxi (CN); Nandi Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 113 days.

(21) Appl. No.: 16/288,706

(22) Filed: Feb. 28, 2019

(65) Prior Publication Data

US 2019/0185835 A1 Jun. 20, 2019

Related U.S. Application Data

(63) Continuation of application No. PCT/CN2017/116188, filed on Dec. 14, 2017.

(30) Foreign Application Priority Data

Nov. 30, 2017 (CN) .......................... 201711238196.8

(51) Int. Cl.
*C12N 9/48* (2006.01)
*C12P 21/06* (2006.01)

(52) U.S. Cl.
CPC .............. *C12N 9/485* (2013.01); *C12P 21/06* (2013.01); *C12Y 304/11005* (2013.01)

(58) Field of Classification Search
None
See application file for complete search history.

(56) References Cited

FOREIGN PATENT DOCUMENTS

| CN | 104131059 A | 11/2014 |
| CN | 105018407 A | * 11/2015 |
| CN | 106967773 A | 7/2017 |

* cited by examiner

*Primary Examiner* — Erin M. Bowers
(74) *Attorney, Agent, or Firm* — IPro, PLLC (57) ABSTRACT

The present disclosure discloses methods for high-yield fermentation of recombinant proline aminopeptidase and preparation of debittered rice peptide, belonging to the fields of fermentation technology, enzyme preparation and food additives. The present disclosure utilizes fermentation kinetic analysis to determine the high-yield fermentation method of proline aminopeptidase by recombinant *Bacillus subtilis*, and improve the yield of proline aminopeptidase to reach 174.8 U/mL. Proline aminopeptidase cooperates with alkaline protease and leucine aminopeptidase to hydrolyze rice protein. The free amino acid content is 27.3 times the unhydrolyzed free amino acid content, and the small peptide content below 180 Da in hydrolysate reaches 44.70%. The exposed N-terminal proline residue is fully hydrolyzed, and the free proline content is 1,064.3 times that of the unhydrolyzed free proline content, which increases the degree of rice protein hydrolysis. The method of the present disclosure has a good application prospect in the fields of foods and beverages and processing and utilization of food protein resources.

5 Claims, 9 Drawing Sheets
Specification includes a Sequence Listing.

METHOD FOR HIGH-YIELD FERMENTATION OF RECOMBINANT PROLINE AMINOPEPTIDASE AND PREPARATION OF DEBITTERED RICE PEPTIDE

TECHNICAL FIELD

The present disclosure relates to methods for high-yield fermentation of recombinant proline aminopeptidase and preparation of debittered rice peptide, belonging to the fields of fermentation technologies, enzyme preparation and food additives.

BACKGROUND

The optimization strategy for microbial fermentation culture often starts from the optimization of a medium and the control of a fermentation process. At present, it is impossible to infer and calculate a medium formula and fermentation process control strategy suitable for a certain microorganism from the basic principle of biochemical reaction. Also, the medium and fermentation process control strategies suitable for different microorganisms are different. No single culture method can be suitable for fermentation culture of a variety of microorganisms. Therefore, it is necessary to use small fermentation equipment such as shake flasks and glass jars for a specific microorganism. The most suitable culture method can be selected by combining and optimizing the medium composition, fermentation process control and other fermentation strategies according to a certain experimental design and test method.

At this stage, the fermentation yield of proline aminopeptidase is still relatively low, which cannot meet the needs of industrial preparation. This is also a key factor for the lack of commercial products of proline aminopeptidase. Therefore, how to improve the fermentation yield of proline aminopeptidase by fermentation strategies has become an urgent problem to be solved.

Enzyme preparation refers to a substance with enzymatic properties extracted from living organisms, and has been widely used in various fields such as medicine, chemical industry, food, brewing, etc., and has a wide range of applications. The food processing industry is closely related to people's lives. Enzymes are increasingly used in the food processing industry, and their roles are becoming more and more important, which are greatly reflected in meat processing, deep hydrolysis of proteins and the use as food additives.

Enzyme preparations have become more and more widely used along with the development of society, and the application field of aminopeptidase is also constantly explored. Non-specific aminopeptidase can hydrolyze the N-terminal amino acid residues of a protein or polypeptide in a broad-spectrum method, and can hydrolyze amino acid residues of different kinds of polypeptides or protein N-terminals to release different kinds of amino acids. The highly specific aminopeptidase can hydrolyze the amino acid residues which cannot be hydrolyzed by endoprotease and non-specific exoprotease, and can effectively deepen the degree of proteolysis and improve the nutritional value of the protein hydrolysate. Rice is one of food crops with the most abundant yield in the world. Rice protein, a product processed from rice, is rich in resources, balanced in nutrition and not susceptible to allergies. Therefore, rice protein has a very broad application prospect in the food industry. However, during the deep processing of rice protein, the hydrolysate often exhibits a strong bitter taste, which affects the field of application. How to improve the degree of hydrolysis of rice protein, remove or reduce the bitterness of hydrolysate, and increase the nutritional value of hydrolysate through cooperative degradation of enzymes has become an urgent problem to be solved.

SUMMARY

In order to solve the above problems, under the guidance of fermentation kinetics, the present disclosure relates to the high-yield fermentation of proline aminopeptidase from recombinant *Bacillus subtilis* and the preparation of debittered rice peptide by hydrolyzing rice protein with proline aminopeptidase together with alkaline protease and leucine aminopeptidase. As a result, the proline aminopeptidase production is significantly improved, the hydrolysis degree of the rice protein is improved by the cooperative hydrolysis of multi-enzyme, the bitterness of the hydrolysate is reduced and the nutritional value of the hydrolysate is improved. Meanwhile, the hydrolysate exhibits certain α-glucosidase inhibition. The proline aminopeptidase produced by the disclosure is an aminopeptidase having strict substrate specificity. The present disclosure increases the production of proline aminopeptidase and reduces the cost of downstream separation and preparation of proline aminopeptidase. By using proline aminopeptidase to specifically excise the N-terminal proline residue, the obstacle resulting from further hydrolyzing Pro by some of the less specific aminopeptidases can be removed, and a better cooperative hydrolysis and debittering effect can be achieved.

The present disclosure provides a method for efficiently producing proline aminopeptidase using recombinant *Bacillus subtilis* to increase the proline aminopeptidase yield and reduce the cost of downstream separation and preparation.

The method includes the following steps:

(1) inoculating a seed medium with the activated recombinant *Bacillus subtilis* and culturing by using a rotary constant temperature shaker at a rotational speed of 220 r/min and a culture temperature of 37° C. for 20 h to prepare a seed solution;

(2) inoculating a 5 L fermenter filled with a 3 L fermentation medium with the seed solution at an inoculum size of 5%, introducing sterile air at an aeration rate of 1.5 vvm, wherein the adjustment of rotational speed is 200 rpm from 0 to 6 h, 400 rpm from 6 to 12 h, 500 rpm from 12 to 28 h, and 400 rpm from 28 h to the end of fermentation; the adjustment of pH is no pH control from 0 to 12 h, pH 7.0 from 12 to 16 h, no pH control from 16 to 28 h, and pH 7.0 after 28 h; the adjustment of temperature is 40° C. from the beginning of fermentation to 8 h, 35° C. from 8 to 12 h, and 33° C. from 12 h to the end of fermentation.

The components of the seed medium in the step (1) are 10 g/L sodium chloride, 10 g/L tryptone, and 5 g/L yeast powder. After sterilization, the final concentration reaches 50 μg/mL by adding filter-sterilized kanamycin.

The components of the fermentation medium in the step (2) are 20 g/L glucose, 60 g/L yeast extract, 18.75 g/L fish meal, 3.25 g/L ammonium chloride, 12.54 g/L $K_2HPO_4$, 2.31 g/L $KH_2PO_4$, and 0.1% (v/v) phytic acid, wherein the pH is 7.0. After sterilization, the final concentration reaches 50 μg/mL by adding filter-sterilized kanamycin.

In one embodiment of the present disclosure, the method, in particular, relates to the preparation of an activated recombinant *Bacillus subtilis* by activating a recombinant *Bacillus subtilis* preserved with a glycerol tube at −40° C. on plate twice:

(1) inoculating a seed medium, wherein the volume of the medium is 150 mL and the shake flask used has a volume of 500 mL, and culturing by using a rotary constant temperature shaker at a rotational speed of 220 r/min and a culture temperature of 37° C. for 20 h to prepare a seed solution;

(2) inoculating a 5 L fermenter filled with a 3 L fermentation medium with the seed solution at an inoculum size of 5%, introducing sterile air at an aeration rate of 1.5 vvm, adjusting the pH with 25% ammonia, and using silicone as a defoaming agent;

(3) the adjustment of rotational speed is 200 rpm from 0 to 6 h, 400 rpm from 6 to 12 h, 500 rpm from 12 to 28 h, and 400 rpm from 28 h to the end of fermentation; the adjustment of pH is no pH control from 0 to 12 h, pH 7.0 from 12 to 16 h, no pH control from 16 to 28 h, and pH 7.0 after 28 h; the adjustment of temperature is 40° C. from the beginning of fermentation to 8 h, 35° C. from 8 to 12 h, and 33° C. from 12 h to the end of fermentation.

During the fermentation in the step (3), samples are taken every 4 h to determine the dry weight of the cells, the enzyme activity of intracellular proline aminopeptidase and the enzyme activity of extracellular proline aminopeptidase.

The present disclosure also provides a method for hydrolyzing rice protein, comprising hydrolyzing with alkaline protease, leucine aminopeptidase and proline aminopeptidase in sequence.

The method comprises preparing a rice protein solution having a mass concentration of 5-8%, (1) adding an appropriate amount of alkaline protease, reacting at 40 to 50° C. for 1 to 4 h and in a boiling water bath for 10 to 20 min;

(2) after cooling, continually adding an appropriate amount of leucine aminopeptidase, reacting at 45 to 50° C. for 1 to 4 h and in a boiling water bath for 10 to 20 min; and (3) after cooling, adding an appropriate amount of proline aminopeptidase, reacting at 45 to 50° C. for 2 to 3.5 h and in a boiling water bath for 10 to 20 min.

The additive amount of alkaline protease in the step (1) is 5,000 to 20,000 U/g rice protein.

The additive amount of leucine aminopeptidase in the step (2) is 1,000 to 4,000 U/g rice protein.

The additive amount of proline aminopeptidase in the step (3) is 50 to 200 U/g rice protein.

In one embodiment of the present disclosure, a casein solution is prepared by preparing with pure water, adjusting pH to 9.0 with a base and reacting in a water bath at 90° C. for 30 min.

In one embodiment of the present disclosure, the method specifically comprises: preparing a 5% rice protein solution with pure water, adjusting pH to 9.0 with a base, and reacting in a water bath at 90° C. for 30 min, wherein the base used is a 2 M NaOH solution; and then, (1) adding an appropriate amount of alkaline protease, reacting at 50° C. for 4 h and in a boiling water bath for 15 min;

(2) after cooling, continually adding an appropriate amount of leucine aminopeptidase, reacting at 50° C. for 4 h and in a boiling water bath for 15 min;

(3) after cooling, adding an appropriate amount of proline aminopeptidase, reacting at 50° C. for 2 h and in a boiling water bath for 15 min.

In the reaction of the step (1), samples are taken every 1 hour, and the degree of hydrolysis of rice protein is determined by a formaldehyde titration method.

In the reaction of the step (2), samples are taken every 1 hour, and the degree of hydrolysis of rice protein is determined by a formaldehyde titration method.

After the reaction of the step (3), after cooling, the obtained hydrolysate is centrifuged at 10,000 rpm for 15 min, and the supernatant is taken; the supernatant is diluted with an equal volume of 10% trichloroacetic acid, allowed to stand for 1 h, and then filtered through a needle filter, the filtrate is centrifuged at 10,000 rpm for 10 min, and the supernatant is again taken. The molecular weight distribution of polypeptide and free amino acid analysis are then separately performed. At the same time, the hydrolysate is determined for the α-glucosidase inhibitory effect.

Under the guidance of fermentation kinetic parameters, the present disclosure obtains a high-yield fermentation process condition of proline aminopeptidase; allows such enzyme to hydrolyze cooperatively with alkaline protease and leucine aminopeptidase by using rice protein as a substrate; optimizes the additive amount of alkaline protease and leucine aminopeptidase in rice proteolysis based on the degree of hydrolysis; and determines the amount of proline aminopeptidase based on free Proline.

The disclosure also provides the use of the method in the fields of foods and beverages and the processing and utilization of food protein resources.

The present disclosure also provides a method for purifying the active α-glucosidase inhibitory peptide, comprising centrifuging the hydrolysate at 10,000 rpm for 15 min, taking and freeze-drying the supernatant. The supernatant is dissolved with 20 mM PB buffer at pH 7.5, subjected to Hi Trip DEAE FF anion exchange chromatography at a flow rate of 1 mL/min, stepwise eluted with 150 mM, 350 mM, and 550 mM NaCl with 10 column volumes at each stage, and the eluate is collected, fully dialyzed, and concentrated by freeze-drying. The freeze-dried powder is rehydrated, and the α-glucosidase inhibition rate of each peak is determined. The fraction with high inhibition rate is subjected to Sephadex G-15 gel chromatography. Collection is conducted by each peak, concentrated by freeze-drying, and rehydrated to determine the α-glucosidase inhibition rate.

Beneficial Effects of the Disclosure

The present disclosure determines the high-yield fermentation process conditions of proline aminopeptidase by recombinant *Bacillus subtilis* under the guidance of fermentation kinetic parameters, that is, the adjustment of rotational speed is 200 rpm from 0 to 6 h, 400 rpm from 6 to 12 h, 500 rpm from 12 to 28 h, and 400 rpm from 28 h to the end of fermentation; the adjustment of pH is no pH control from 0 to 12 h, pH 7.0 from 12 to 16 h, no pH control from 16 to 28 h, and pH 7.0 after 28 h; the adjustment of temperature is 40° C. from the beginning of fermentation to 8 h, 35° C. from 8 to 12 h, and 33° C. from 12 h to the end of fermentation. The optimized yield of proline aminopeptidase reaches 174.8 U/mL, which is 1.66 times the highest level before optimization.

The enzyme hydrolyzes rice protein by cooperating with alkaline protease and leucine aminopeptidase, and the additive amount of alkaline protease is determined as 15,000 U/g rice protein and hydrolysis time is determined as 4 h; the additive amount of leucine aminopeptidase is determined as 3,000 U/g rice protein and hydrolysis time is determined as 2 h. After the cooperative hydrolysis of the three enzymes, the free amino acid content is 3.484 mg/mL, which is 27.4 times the unhydrolyzed free amino acid content. The hydrolysate mainly exists as small peptide and free amino acid, and the content of small peptide below 180 Da reaches 44.70%. The exposed N-terminal proline residue is fully hydrolyzed, and the free proline content is 0.149 mg/mL, which is 1,064.3 times the unhydrolyzed free proline content. The hydrophobic amino acid content in the hydrolysate is significantly increased, the bitterness of hydrolysate is reduced, the degree of rice protein hydrolysis is deepened, the nutritional value of the hydrolysate is improved, and a component with strong inhibitory activity is obtained by isolating and purifying the active α-glucosidase inhibitory peptide in the hydrolysate, which has a good application prospect in functional and health foods and beverages.

BRIEF DESCRIPTION OF FIGURES

FIG. 2A-2F: Analysis of fermentation kinetics under different conditions (FIG. 2A: 1: 200 rpm, 2: 300 rpm, 3: 400 rpm, 4: 500 rpm, FIG. 2B: 1: 200 rpm, 2: 300 rpm, 3: 400 rpm, 4: 500 rpm; FIG. 2C: 1: no pH control, 2: pH 7.0, 3: pH 7.5, FIG. 2D: 1: no pH control, 2: pH 7.0, 3: pH 7.5; FIG. 2E: 1: 30° C., 2: 33° C., 3: 35° C., 4: 37° C., 5: 40° C., FIG. 2F: 1: 30° C., 2: 33° C., 3: 35° C., 4: 37° C., 5: 40° C.).

DETAILED DESCRIPTION

Biomaterial sample: the purification and preparation of recombinant *Bacillus subtilis* (*Bacillus subtilis* WB600, a recombinant strain of histidine-tagged proline aminopeptidase, and the plasmid used is PMA5) and proline aminopeptidase are described in Chinese patent No. CN105925650A.

Method for determination of proline aminopeptidase activity: using L-proline p-nitroaniline as a substrate (a substrate stock solution is prepared with Tris-HCl 7.5 at a concentration of 4.25 mM), reacting a reaction mixture including 1 mL of enzyme solution as diluted, 2 mL of Tris-HCl 7.5 buffer and 1 mL of substrate stock solution in a water bath at 50° C. for 10 min, adding 1 mL of 50% (v/v) glacial acetic acid solution to terminate the reaction, and measuring the absorbance at 405 nm.

The enzyme activity unit (U) is defined as the amount of enzyme required to decompose L-proline p-nitroaniline to produce 1 μM of p-nitroaniline at 50° C. per minute.

The enzyme activity unit of alkaline protease is defined as the amount of enzyme required to hydrolyze casein to produce 1 μg of tyrosine per minute at 40° C.

The enzyme activity unit of leucine aminopeptidase is defined as the amount of enzyme required to decompose L-leucine p-nitroaniline to produce 1 μM of p-nitroaniline at 50° C. per minute.

Fermentation tank used: T&J Type A 5 L fermenter (T&J Bio-engineering (Shanghai) Co., LTD)

Detection of polypeptide molecular weight distribution: Waters 600 high performance liquid chromatographic instrument (equipped with a 2487 UV detector and an Empower workstation).

Determination of free amino acids in the hydrolysate: the determination is carried out by using an amino acid chromatographic instrument (Agilent 1100).

Determination of α-glucosidase inhibition rate: preparing 1.5 U/mL α-glucosidase solution with potassium phosphate buffer at pH 6.8, mixing 70 μL of the enzyme solution with 70 μL of the sample, incubating in a water bath at 37° C. for 10 min, and then adding 70 μL of potassium phosphate buffer at pH 6.8 containing 10 mM pNPG, reacting in a water bath at 37° C. for 1 h. After that, 70 μL of 1 M $Na_2CO_3$ solution is added to terminate the reaction. Absorbance A is measured at 405 nm. The α-glucosidase inhibition rate is calculated as follows:

$$\text{Inhibition rate} = \left(1 - \frac{A_i - A_j}{A_0}\right) \times 100\%,$$

wherein $A_0$ is the control, $A_i$ is the absorbance of sample, and $A_j$ is the absorbance of sample control.

Example 1: Fermentation Culture of Recombinant *Bacillus subtilis* Under Different Rotational Speeds A seed medium was inoculated with the recombinant *Bacillus subtilis* preserved with a glycerol tube at −40° C., and cultured by using a rotary constant temperature shaker at a rotational speed of 220 r/min and a culture temperature of 37° C. for 20 h. A 5 L fermenter filled with a 3 L fermentation medium was inoculated with the seed solution at an inoculum size of 5%, and sterile air was introduced at an aeration rate of 1.5 vvm during the fermentation process. The fermentation temperature was 37° C., pH 7.0. The rotational speed was set at 200 rpm, 300 rpm, 400 rpm, 500 rpm respectively, and the fermentation time was 36 h. During the fermentation, samples were taken every 2 h to measure the dry weight of the cells, the activity of extracellular proline aminopeptidase and the activity of intracellular proline aminopeptidase, etc.

Figure 1:
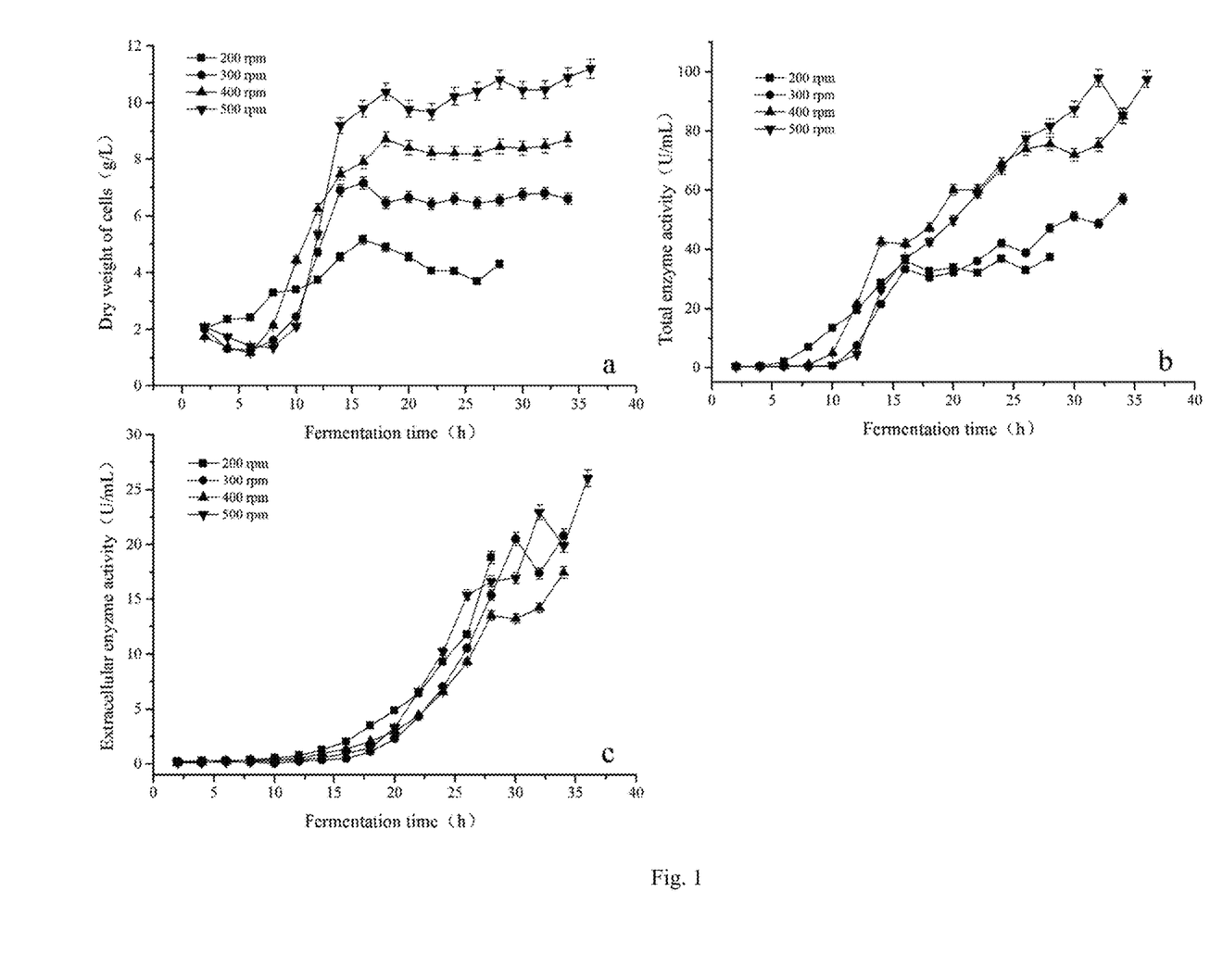
FIG. 1: Effect of rotational speed on fermentation of recombinant bacteria.

As shown in FIG. 1, the rotational speed was increased from 200 rpm to 500 rpm, and the proline aminopeptidase activity was also increased from 38.0 U/mL to 97.5 U/mL.

Example 2: Fermentation Culture Under the Guidance of Fermentation Kinetics

A 5 L fermenter filled with a 3 L fermentation medium was inoculated with the seed solution at an inoculum size of 5%, and sterile air was introduced at an aeration rate of 1.5 vvm during the fermentation process. The specific growth rate ($\mu_{cell}$) and specific PAP production rate ($\rho_{PAP}$) were analyzed based on fermentation kinetics.

Figure 2A:
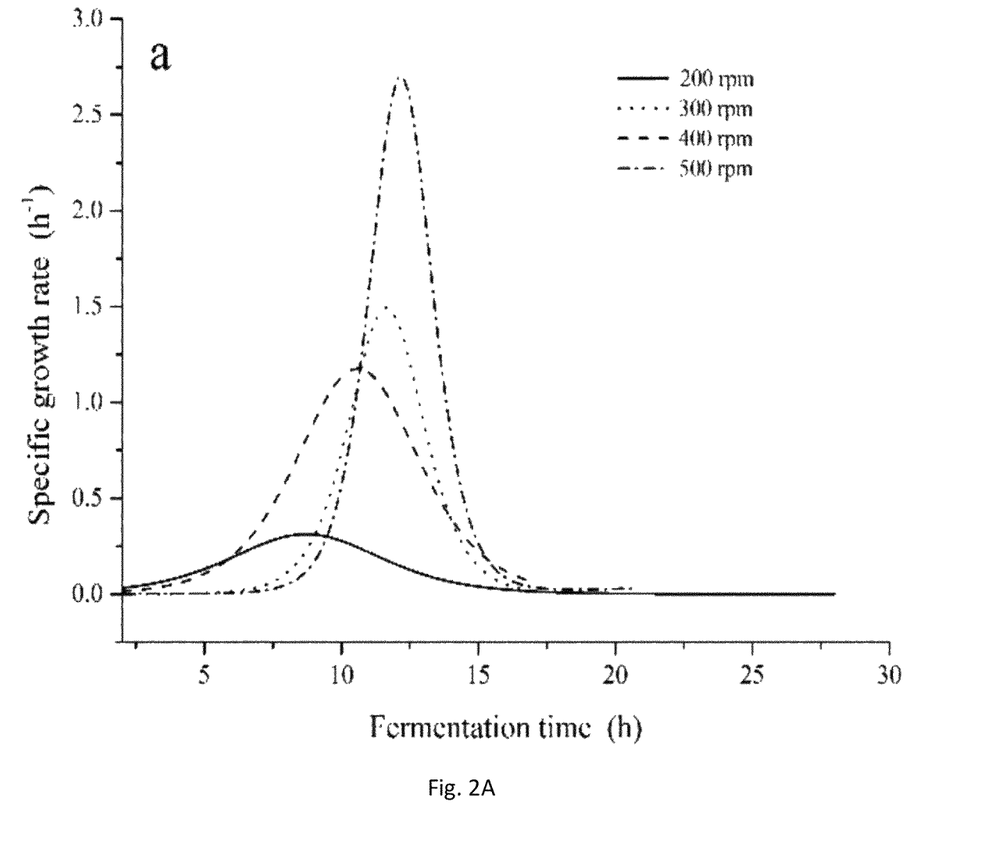
Figure 2B:
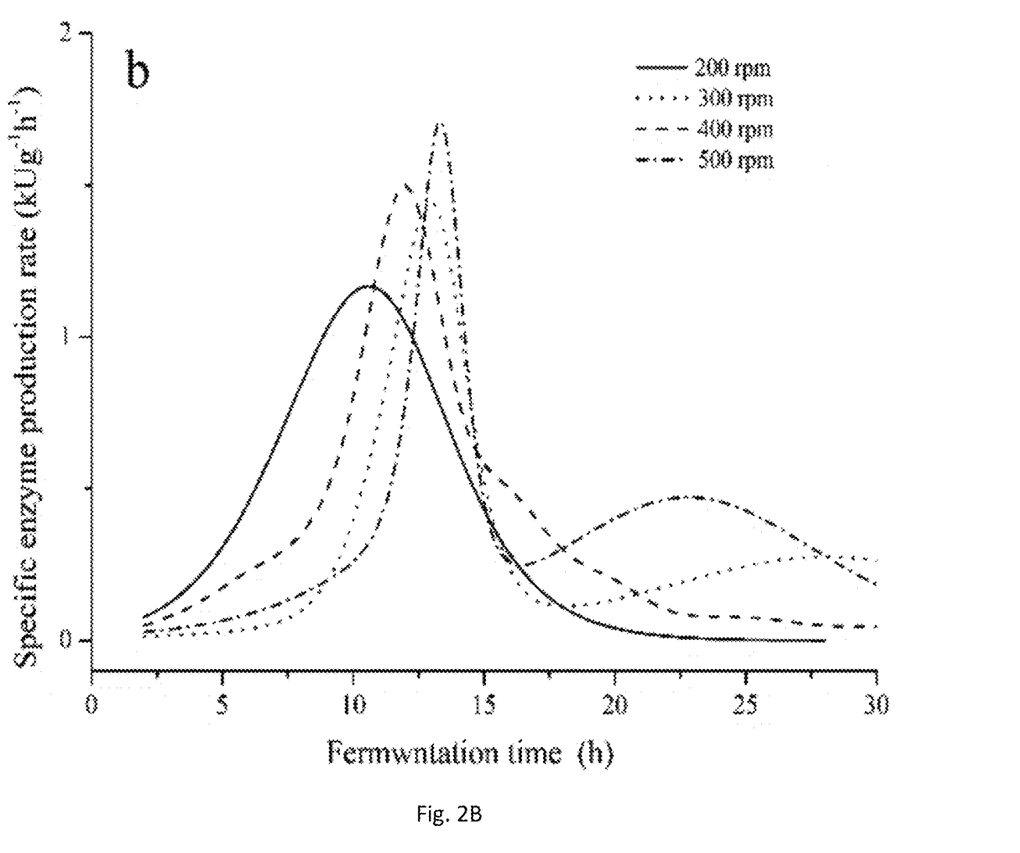

As shown in FIGS. 2A and 2B, the $\mu_{cell}$ reached a maximum under an agitation speed of 200 rpm during the first 6 h of fermentation culture; the $\rho_{PAP}$ reached the highest value when the agitation speed was set at 400 rpm, and the $\mu_{cell}$ was maintained at higher level from 6 h to 12 h; the $\rho_{PAP}$ reached the maximum at 500 rpm from 12~28 h and at 400 rpm after 28 h.

Figure 2C:
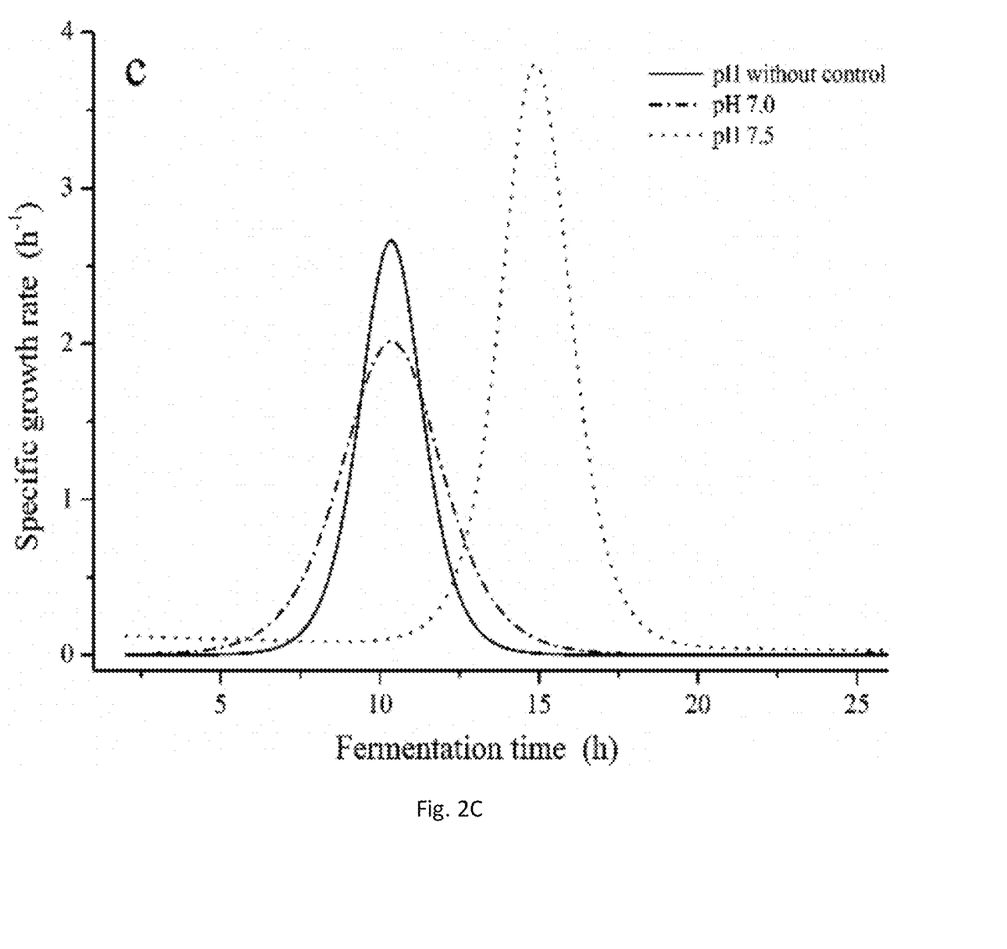
Figure 2D:
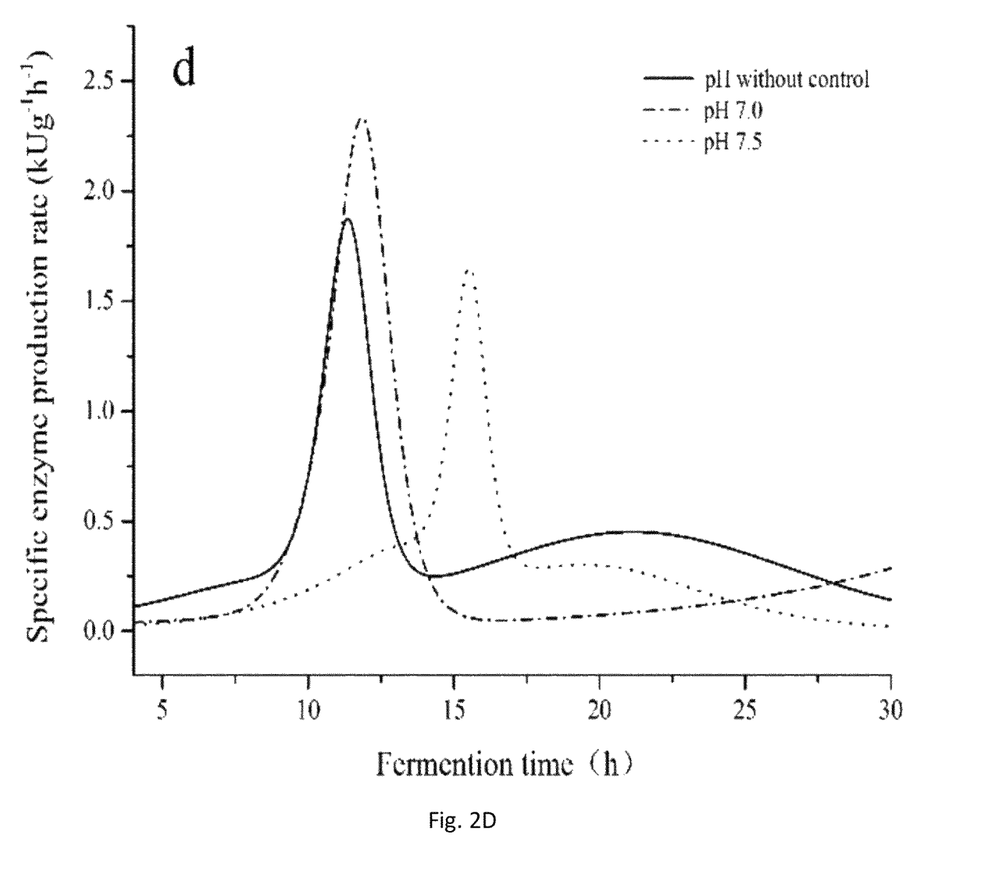

FIGS. 2C and 2D show that the change of $\mu_{cell}$ and $\rho_{PAP}$ at different pH values. Recombinant *B. subtilis* had a longer log phase at pH 7.5 that was adverse to cell growth; the $\mu_{cell}$ reached the maximum without pH control during the first 12 h of fermentation; however, $\rho_{PAP}$ reached the maximum at pH 7.0 from 12~14 h; from 14~28 h, $\rho_{PAP}$ reached the maximum without pH control, and pH 7.0 was beneficial for PAP production after 28 h.

Figure 2E:
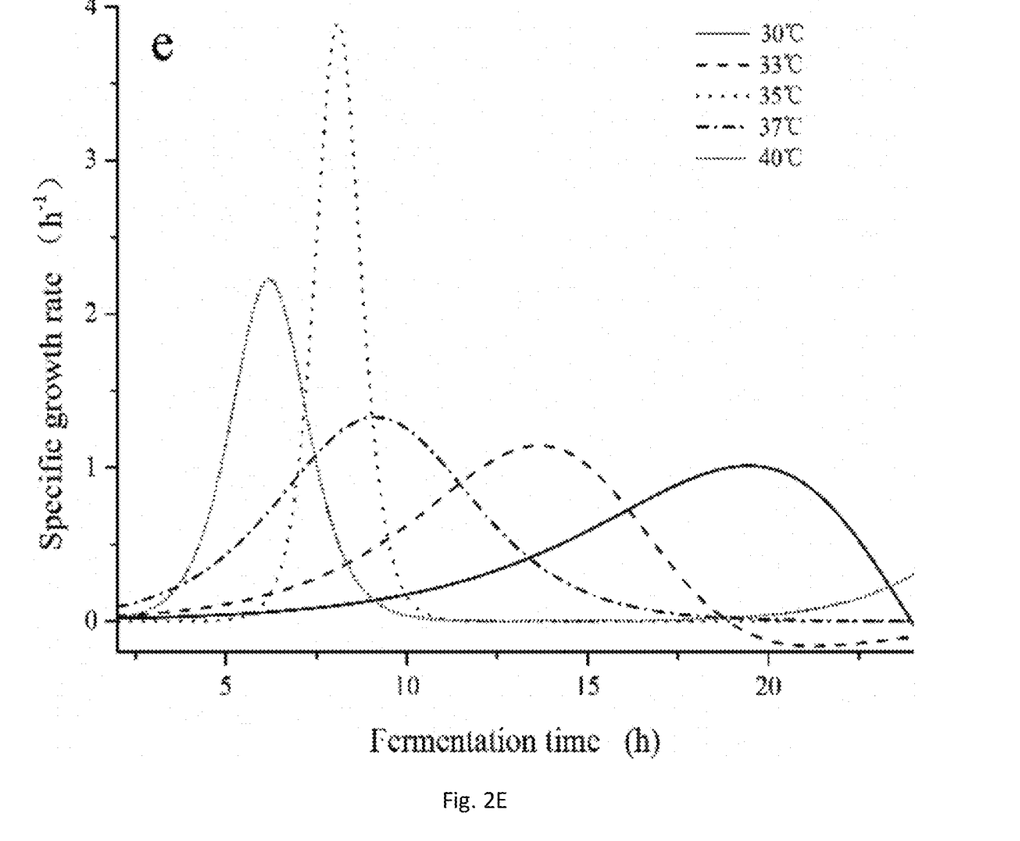
Figure 2F:
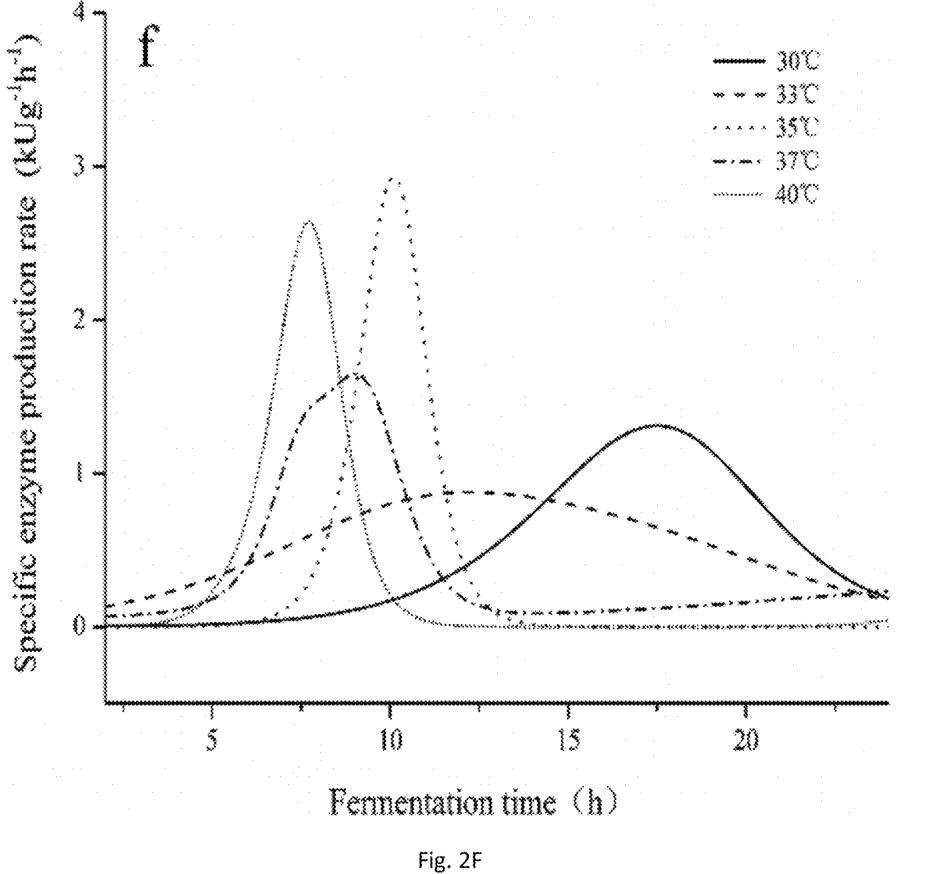

FIGS. 2E and 2F show the effect of temperature on $\mu_{cell}$ and $\rho_{PAP}$ during the fermentation process. The recombinant *B. subtilis* quickly reached $\mu_{max}$ at 40° C. in the first 8 h of fermentation; the $\mu_{cell}$ reached the maximum and $\rho_{PAP}$ was maintained at a higher level at 35° C. from 8~12 h, and $\rho_{PAP}$ continuously maintained a higher level at 33° C. after 12 h.

The fermentation conditions are listed as follows: the adjustment of rotational speed was 200 rpm from 0 to 6 h, 400 rpm from 6 to 12 h, 500 rpm from 12 to 28 h, and 400 rpm from 28 h to the end of fermentation; the adjustment of pH was no pH control from 0 to 12 h, pH 7.0 from 12 to 16 h, no pH control from 16 to 28 h, and pH 7.0 after 28 h; the adjustment of temperature was 40° C. from the beginning of fermentation to 8 h, 35° C. from 8 to 12 h, and 33° C. from 12 h to the end of fermentation. During the fermentation, samples were taken every 4 h to measure the dry weight of the cells, the activity of extracellular proline aminopeptidase and the activity of intracellular proline aminopeptidase, etc.

Figure 3:
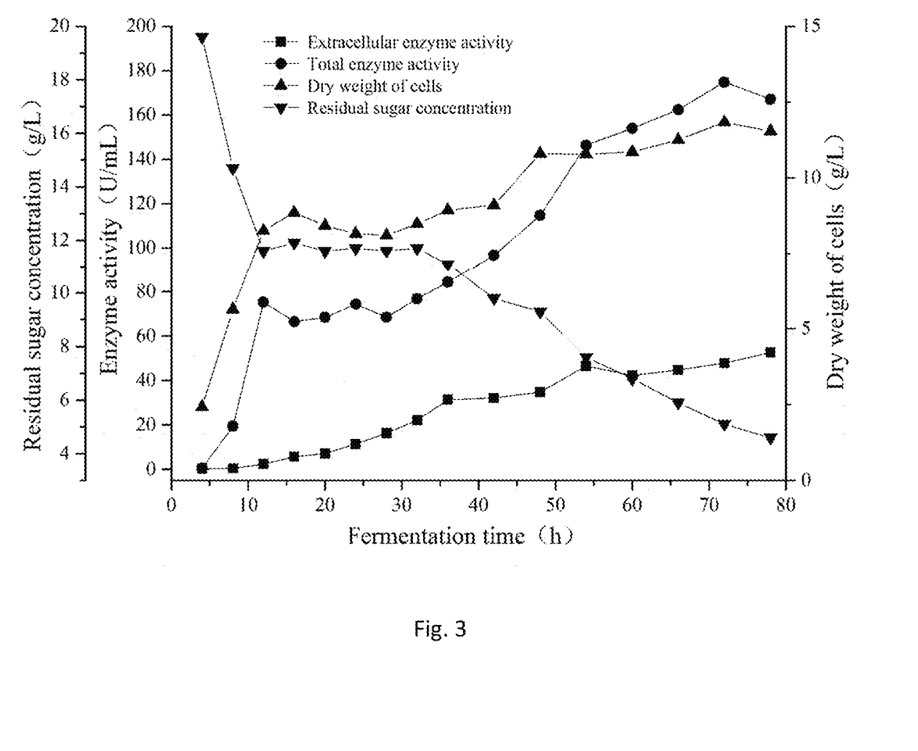
FIG. 3: Determining a fermentation process curve under a fermentation process.

As shown in FIG. 3, the fermentation strategy under kinetic analysis could significantly increase the yield of proline aminopeptidase, and the proline aminopeptidase activity reached 174.8 U/mL.

Example 3 : Role of Proline Aminopeptidase from Recombinant *Bacillus subtilis* in Rice Protein Hydrolysis 5% rice protein solution was prepared with pure water buffer and pH was adjusted to 9.0 with a 2M NaOH solution. The mixture was incubated in a water bath at 90° C. for 30 min. After cooling, alkaline protease was added in an amount of 15,000 U/g rice protein, and the reaction was performed at 50° C. for 4 h and in a boiling water bath for 15 min. After cooling, leucine aminopeptidase powder was continually added in an amount of 3,000 U/g rice protein, and the reaction was performed at 50° C. for 2 h and in a boiling water bath for 15 min. After cooling, the enzyme solution of recombinant proline aminopeptidase was then added in an amount of 200 U/g rice protein, the reaction was performed at 50° C. for 2 h and in a boiling water bath for 15 min, and cooled. The hydrolysate was mainly in the form of small peptides and free amino acids. The content of small peptides below 180 Da reached 44.70%, and the exposed N-terminal proline residues were fully hydrolyzed. The free proline content was 0.149 mg/mL, which was 1064.3 times the unhydrolyzed free proline content.

Figure 4:
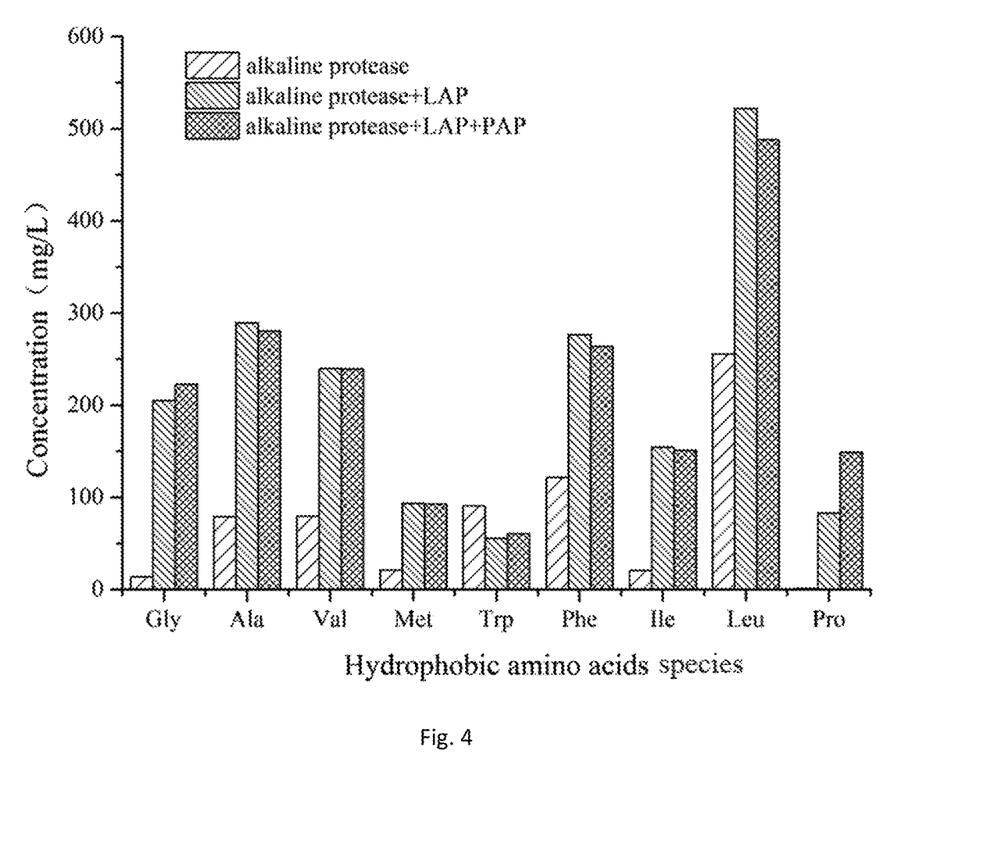
FIG. 4: Hydrophobic amino acid in hydrolysate.

In addition, the inventors also compared the effects of different enzymatic hydrolysis methods on the hydrolysis effect of rice protein, and the results were shown in Table 1 and FIG. 4. The results showed that the content of small peptides below 180 Da was 13.68% when the hydrolysis was carried out by alkaline protease alone, and the content of small peptides below 180 Da was 42.21% when the hydrolysis was carried out by both alkaline protease and leucine aminopeptidase.

TABLE 1

Effect of different enzymatic hydrolysis methods on the hydrolysis effect of rice protein

| Molecular weight | Mass ratio of small peptide having respective molecular weight (%) | | | |
| --- | --- | --- | --- | --- |
| (Da) | 1 | 2 | 3 | 4 |
| >5000 | — | 0.38 | 2.95 | 2.33 |
| 5000-3000 | 1.4 | 1.00 | 1.34 | 1.41 |
| 3000-2000 | 2.96 | 1.86 | 1.65 | 1.77 |
| 2000-1000 | 11.61 | 7.32 | 5.08 | 5.25 |
| 1000-500 | 26.16 | 18.26 | 11.06 | 10.92 |
| 500-180 | 48.85 | 57.50 | 35.70 | 33.63 |
| <180 | 9.03 | 13.68 | 42.21 | 44.70 |

Note:
1: rice protein solution, 2: hydrolysate obtained by alkaline protease alone, 3: hydrolysate obtained by both alkaline protease and leucine aminopeptidase, 4: hydrolysate obtained cooperatively by synergy of proline aminopeptidase, alkaline protease and leucine aminopeptidase.

In addition, the free amino acid content obtained by the method of the present disclosure was 3.484 mg/mL, which was 27.4 times the unhydrolyzed free amino acid content, wherein the proline content was 1,064.3 times the unhydrolyzed proline content, and the hydrophobic amino acid content was significantly improved. When the hydrolysis was carried out by alkaline protease alone, the free amino acid content was 1.121 mg/mL. When the hydrolysis was carried out by both the alkaline protease and leucine aminopeptidase, the free amino acid content was 3.567 mg/mL, which was basically balanced with the free amino acid content when the hydrolysis was cooperatively carried out by three enzymes; however, the hydrolysate content was 0.083 mg/mL, which was significantly lower the free proline content when the hydrolysis was cooperatively carried out by three enzymes.

According to the present disclosure, the rice protein was cooperatively hydrolyzed by proline aminopeptidase, alkaline protease and leucine aminopeptidase. In the obtained hydrolysate, the content of free amino acid and the content of small peptide were greatly increased, the content of hydrophobic amino acid was also significantly improved, and not only was the degree of hydrolysis of rice protein greatly improved, but also the bitterness of the hydrolysate was removed or reduced.

Example 4: Method for Hydrolyzing Rice Protein

The method for hydrolyzing rice protein of the present disclosure comprised preparing a rice protein solution having a mass concentration of 8%, (1) adding an appropriate amount of alkaline protease, reacting at 40° C. for 3.5 h and in a boiling water bath for 10 min;

(2) after cooling, continually adding an appropriate amount of leucine aminopeptidase, reacting at 45° C. for 3 h and in a boiling water bath for 10 min;

(3) after cooling, adding an appropriate amount of proline aminopeptidase, reacting at 45° C. for 3 h and in a boiling water bath for 10 min, wherein the additive amount of alkaline protease was 20,000 U/g rice protein; the additive amount of leucine aminopeptidase was 4,000 U/g rice protein; and the additive amount of proline aminopeptidase was 100 U/g rice protein.

The polypeptide more than 2,000 Da in the obtained rice protein hydrolysate was basically absent, while the small peptide content below 180 Da reached 48.26%, the free amino acid content was 5.852 mg/mL, and the free proline content is 1,136.4 times the unhydrolyzed free proline content.

Example 5: Method for Separating and Purifying Active α-Glucosidase Inhibitory Peptide 50 mL of rice protein hydrolysate cooperatively hydrolyzed by alkaline protease, leucine aminopeptidase and proline aminopeptidase was centrifuged at 10,000 rpm for 15 min, and the supernatant was taken and freeze-dried. The freeze-dried powder was dissolved in 20 mM pH 7.5 PB buffer, and preliminary separation was performed by Hi Trip DEAE FF anion exchange chromatography. The loading volume was 10 mL, the flow rate was 1 mL/min, and the stepwise elution was performed with 150 mM, 350 mM, and 550 mM NaCl solution. 10 column volumes were eluted at each stage, and the eluate was collected, fully dialyzed, and concentrated by freeze-drying. The freeze-dried powder was rehydrated, and the α-glucosidase inhibition rate and the polypeptide concentration of each elution peak were determined. The elution peak $F_4$ fraction was found to have the highest inhibition rate. The fraction was subjected to Sephadex G-15 gel chromatography, the loading volume was 1 mL, and the flow rate was 0.5 mL/min. Collection is conducted by each peak and the eluted peaks were freeze-dried. The freeze-dried powder was dissolved in 1 mL of pure water, and the α-glucosidase inhibition rate and the polypeptide concentration were determined. The $F_4$ b fraction having the most potent α-glucosidase inhibitory effect was obtained, which had an $IC_{50}$ of 132.6 μg/mL.

Although the present disclosure has been disclosed in the above preferred embodiments, the present disclosure is not limited thereto, and various modifications and changes can be made without departing from the spirit and scope of the disclosure by anyone familiar with this technology. Therefore, the protection scope of the present disclosure should be determined by the claims.

*lis*, wherein the recombinant *Bacillus subtilis* comprises a gene encoding the proline aminopeptidase, comprising:
(1) inoculating a seed medium with the recombinant *Bacillus subtilis* and culturing to prepare a seed solution;
(2) inoculating a fermentation medium with the seed solution, introducing sterile air at an aeration rate of 1.2 to 1.5 vvm, wherein rotational speed is adjusted as: 200 rpm from 0 to 6 h, 400 rpm from 6 to 12 h, 500 rpm from 12 to 28 h, and 400 rpm from 28 h to the end of fermentation; wherein adjustment of pH is: applying no pH control from 0 to 12 h, setting pH as 7.0 from 12 to

What is claimed is:

1. A method for high-yield fermentation production of a proline aminopeptidase using a recombinant *Bacillus subti-*

16 h, applying no pH control from 16 to 28 h, and setting pH as 7.0 after 28 h; and wherein temperature is adjusted as: 40° C. from the beginning of fermentation to 8 h, 35° C. from 8 to 12 h, and 33° C. from 12 h to the end of fermentation.

2. The method of claim 1, wherein the step (2) comprises inoculating a 5 L fermenter with the seed solution at an inoculum size of 5%, wherein the 5 L fermenter is filled with a 3 L fermentation medium.

3. The method of claim 1, wherein the seed medium in the step (1) comprises: 10 g/L sodium chloride, 10 g/L tryptone, and 5 g/L yeast powder, and wherein after sterilization, and wherein final concentration reaches 50 μg/mL by adding filter-sterilized kanamycin.

4. The method of claim 1, wherein the fermentation medium in the step (2) comprises 20 g/L glucose, 60 g/L yeast extract, 18.75 g/L fish meal, 3.25 g/L ammonium chloride, 12.54 g/L $K_2HPO_4$, 2.31 g/L $KH_2PO_4$, and 0.1% (v/v) phytic acid, wherein the pH is 7.0.

5. The method of claim 1, wherein the step (2) comprises inoculating a 5 L fermenter filled with a 3 L fermentation medium with the seed solution at an inoculum size of 5% and introducing sterile air at an aeration rate of 1.5 vvm, adjusting the pH with 25% ammonia, and using silicone as a defoaming agent.

* * * * *

SEQUENCE LISTING

<160> NUMBER OF SEQ ID NOS: 1

<210> SEQ ID NO 1
<211> LENGTH: 1344
<212> TYPE: DNA
<213> ORGANISM: Artificial Sequence
<220> FEATURE:
<223> OTHER INFORMATION: Synthetic DNA

<400> SEQUENCE: 1

```
atggctgcca aactagtaga caagaagctt cacaacgtcc cagggaagct ccgtgtagca      60
gaactgctct tgacgttcc agtcaactac agccggccaa atgatggcac tttgaggctt     120
tttgcccgca gtgttcggcg tttgacgact tcatttgatg ctccaaagga ggacaagcaa     180
ctgccttggc ttgtatacct acagggtgga cctggttatg gatgtcgacc tcctcaggag     240
aatggctgga ttggcaccgc ccttgacaag ggataccagg ttctgtttct agatcaacgt     300
ggcactggcc tcagctccac gatcagtgca ggtacccttg ccttgaaagg caatgcaatc     360
aagcaggcga agtacctgaa gaacttccga gccgataaca ttgtcagaga ttgtgaagcc     420
gttcgccgtt gccttaccgt ggactatccc gaagataaac gtaaatggag tattatcggc     480
cagagtttcg gtggtttctg cgctgtgacg tatctttcta tgttcccaga ggggttagcg     540
gaagcgttta tttgcggcgg attgcctcct cttgtcaatg atcctgaccc agtctatgca     600
cggacatacg aaaagctgga ggagcgaaac aaggcctatt actccaagtt ccctgaagat     660
gttgagagag tcaagagaat catgcagtat ctcgaggaga acgatgtttc tgttccgtcc     720
gggagactga cacccgcgag attccagcaa ttgggtctga tatttggcat gcacggtggc     780
cttgatagta tccacgagct tgttctgcgc gcctggaatg atctcgagat ctttggcttc     840
ctgactcatc ctacgcgcac ttcaatcgat gccgcaggtg gctttgatgg tgctgttatt     900
tatgccattc ttcacgaatc tatctattgc caagggcaag cttcaaactg gtctgcggat     960
agacttcgtt cggccaatgc gaacttcagc attgatgcca gccgaccaga gatctggttt    1020
acgggcgaaa tgatttacaa ggacatgttc gactcgtacg acgagctcaa cgagatcaag    1080
gaggcggcag acatcctcgc aactaccaag gactggcctg cgctctatga cgaggcccag    1140
ctggcgaaga atgaagttcc tgtctacgct gctacgtaca tagatgacat gtacgtgcac    1200
ttcagtcatg cctcaaatac ggctgcgaag atcaagggta tcaaacagtt cattacgaat    1260
accatgtatc ataatgctct ccgagctaag tcggatgagg ttatgcagca gcttttttgcc    1320 ttgagggacg actctattga ttag                                           1344
```